United States Patent [19]

Weber

[11] 4,424,170
[45] Jan. 3, 1984

[54] HALOSTILBENE SULFONATES USEFUL AS STARTING MATERIALS FOR MAKING FLUORESCENT WHITENING AGENTS OF THE 4,4'-DISTYRYLBIPHENYL SERIES

[75] Inventor: Kurt Weber, Basel, Switzerland

[73] Assignee: Ciba-Geigy Corporation, Ardsley, N.Y.

[21] Appl. No.: 375,607

[22] Filed: May 6, 1982

[30] Foreign Application Priority Data

May 14, 1981 [CH] Switzerland .......................... 3143/81

[51] Int. Cl.³ .................. C07C 143/29; C07C 143/36
[52] U.S. Cl. ............................. 260/505 C; 260/512 C
[58] Field of Search ............ 260/505 C, 512 C, 501.9, 260/501.21

[56] References Cited

U.S. PATENT DOCUMENTS 3,984,399 10/1976 Weber et al. ................... 260/505 C
4,285,885 8/1981 Weber .............................. 260/505 C

FOREIGN PATENT DOCUMENTS 3001876 7/1981 Fed. Rep. of Germany ... 260/505 C

Primary Examiner—Nicky Chan
Attorney, Agent, or Firm—Edward McC. Roberts

[57] ABSTRACT

The invention relates to stilbene compounds of the formula

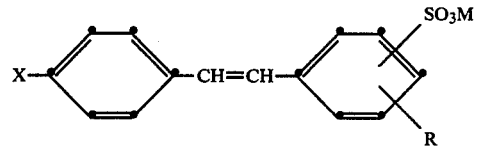

wherein X is halogen, R is hydrogen, —SO$_3$M, halogen, C$_1$–C$_4$ alkyl or C$_1$–C$_4$ alkoxy and M is hydrogen or a salt-forming cation. These compounds are starting materials for obtaining known fluorescent whitening agents of the 4,4'-distyrylbiphenyl series.

5 Claims, No Drawings

HALOSTILBENE SULFONATES USEFUL AS STARTING MATERIALS FOR MAKING FLUORESCENT WHITENING AGENTS OF THE 4,4'-DISTYRYLBIPHENYL SERIES

The present invention relates to novel stilbene compounds, to a process for their production, and to the use thereof as intermediates for obtaining fluorescent whitening agents of the distyrylbiphenyl series.

The preparation of 4,4'-distyrylbiphenyls from 4,4'-dialkoxyphosphorylmethylbiphenylenes and benzaldehydes by the Horner-Wittig synthesis is known from U.S. patent specification No. 3,984,399. The methanephosphonates used as starting materials are obtained from 4,4'-bis-chloromethylbiphenyl, which in turn is obtained by chloromethylation of biphenyl. This reaction, however, results in the formation of chloromethylbiphenyls as by-products which are strong skin irritants.

It is the object of the present invention to provide starting materials for the production of fluorescent whitening agents of the 4,4'-distyrylbiphenyl series, which starting materials do not have the shortcomings referred to above.

The stilbene compounds of this invention have the formula

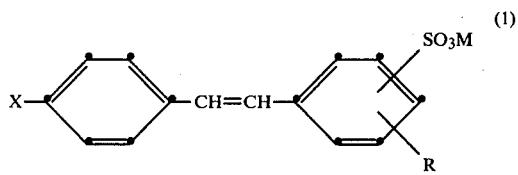
(1)

wherein X is halogen, R is hydrogen, —SO₃M, halogen, $C_1$–$C_4$alkyl or $C_1$–$C_4$alkoxy, and M is hydrogen or a salt-forming cation.

Suitable halogens X and R are chlorine, bromine and fluorine, with chlorine and bromine being preferred.

Examples of salt-forming cations M are alkali metal ions, ammonium ions or amine salt ions. Preferred amine salt ions are those of the formula H⊕ NR₁°R₂°R₃°, in which each of R₁°, R₂° and R₃° independently of the other is hydrogen, alkyl, alkenyl, hydroxyalkyl, cyanoalkyl, haloalkyl or phenylalkyl, or in which R₁° and R₂° together complete a 5- to 7-membered, saturated nitrogen-containing heterocyclic ring system which may additionally contain a further nitrogen or oxygen atom as ring member, e.g. a piperidine, piperazine, pyrrolidine, imidazoline or morpholine ring, and R₃° is hydrogen.

Preferred stilbene compounds of the formula (1) are those of the formula

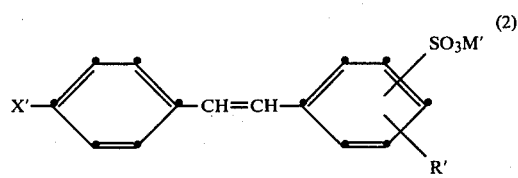
(2)

wherein X' is chlorine or bromine, R' is hydrogen, —SO₃M', chlorine, bromine, $C_1$–$C_4$alkyl or $C_1$–$C_4$alkoxy, and M' is an alkali metal ion, an ammonium ion or an amine salt ion.

Particularly interesting stilbene compounds are those of the formula

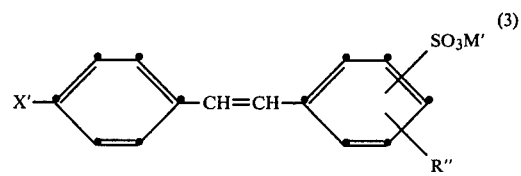
(3)

wherein X' is chlorine or bromine, R" is hydrogen, chlorine, methyl or methoxy, and M' is an alkali metal ion, an ammonium ion or an amine salt ion.

The most preferred stilbene compounds are those of the formulae

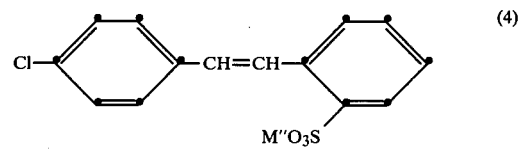
(4)

and

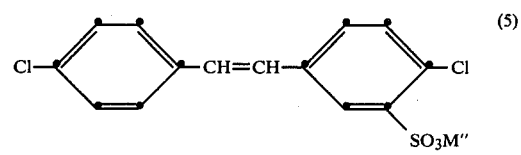
(5)

wherein M" is sodium or potassium.

The stilbene compounds of the formula (1) can be obtained in a manner known per se by reacting one mole of a compound of the formula

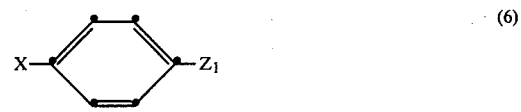
(6)

with one mole of a compound of the formula

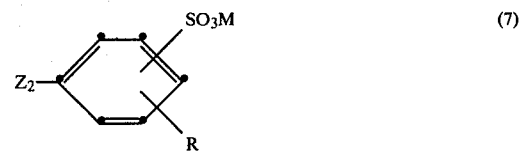
(7)

in the presence of a strong base and of a polar solvent, in which formulae one of the symbols Z₁ and Z₂ is a HOC group and the other is a group of the formula

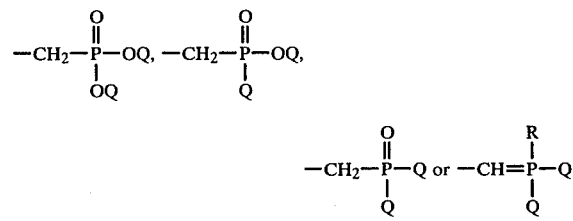

wherein Q is an unsubstituted or substituted alkyl radical of 1 to 6 carbon atoms, an aryl radical, preferably a phenyl radical, a cycloalkyl radical, preferably a cyclohexyl radical, or an aralkyl radical, preferably a benzyl radical.

The compounds of the formula (1) are preferably obtained by reacting 1 mole of a compound of the formula

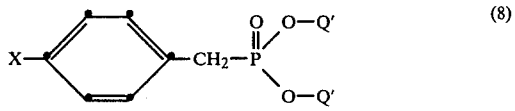
(8)

wherein X is as defined above, and Q' is $C_1$–$C_4$alkyl, in the presence of a strong base and of a polar solvent, with one mole of a compound of the formula

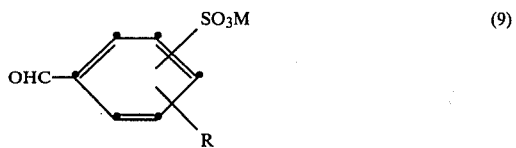
(9)

wherein M and R are as defined above.

Suitable solvents are e.g. alcohols such as methanol, ethanol, isopropanol, butanol, glycols, glycol ethers such as 2-methoxyethanol, hexanols, cyclohexanol and cyclooctanol, and also ethers such as diisopropyl ether, tetrahydrofurane and dioxane, as well as dimethyl sulfoxide, formamide and N-methylpyrrolidone. Particularly suitable solvents are polar organic solvents such as dimethyl formamide and dimethyl sulfoxide. Several of the reactions can also be carried out in aqueous solution.

The temperature at which the reaction is conducted may vary within wide limits and depends on:
- (α) the stability of the solvent employed to the reactants, especially to the strongly basic alkali metal compounds,
- (β) the reactivity of the condensation partners, and
- (γ) the effectiveness of the combination of solvent and base as condensing agent.

In practice, temperatures normally in the range from about 10° to 100° C. are suitable, especially if dimethyl formamide or dimethyl sulfoxide is employed as solvent. The preferred temperature range is from 20° to 60° C.

Suitable strong bases are, in particular, the hydroxides, amides and alcoholates (preferably those of primary alcohols containing 1 to 4 carbon atoms) of alkali metals, those of lithium, sodium and potassium being of principal interest for economic reasons. In principle, however, and in special cases, it is also possible to use with success alkali metal sulfides and alkali metal carbonates, aryl alkali compounds, e.g. phenyllithium, or strongly basic amines (including ammonium bases), e.g. trialkylammonium hydroxides.

The stilbene compounds of the formula (1) can be used for obtaining, in a manner which is known per se, known fluorescent whitening agents of the 4,4'-distyrylbiphenyl series, e.g. those described in U.S. patent specification No. 3,984,399.

The preparation of such fluorescent whitening agents comprises subjecting 2 molar equivalents of a stilbene compound of the formula (1) to a reductive arylation, e.g. in accordance with the following reaction scheme:

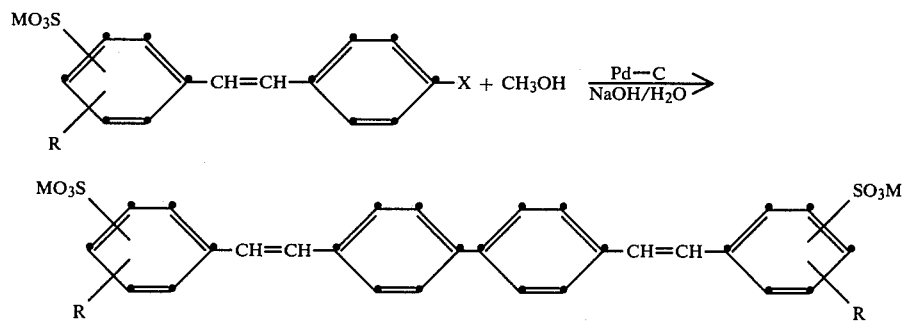

wherein X, R and M are as defined above.

The following Examples illustrate the invention in more detail, but without implying any restriction to what is described therein. Percentages are by weight, unless otherwise indicated.

EXAMPLE 1

530 g of diethyl(4-chlorophenyl)methanephosphonate (98.8%) and 442 g of the sodium salt of benzaldehyde-2-sulfonic acid (94%) are dissolved, with stirring, in 2000 ml of dimethyl formamide. Then 396 g of a 30% methanolic solution of sodium methylate are added dropwise over 70 minutes, whereupon the temperature rises to 50° C. The reaction mixture is then stirred for 20 hours at room temperature, neutralised with hydrochloric acid and evaporated to dryness in vacuo. The residue is dissolved at 90° C. in 500 ml of demineralised water, the solution is cooled, and the crystallised precipitate is filtered with suction and vacuum dried at 110° C. This crude product is first recrystallised from 6 liters of anhydrous alcohol and then from 250 ml of demineralised water and vacuum dried at 110° C. Yield: 387 g of the compound of the formula

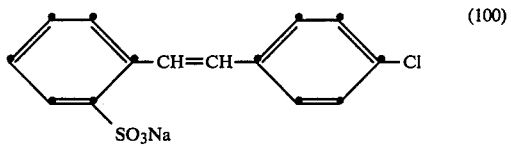
(100)

in the form of white needles which still contain 0.29 mole of water of crystallisation. UV spectrum: $\lambda_{max.}=302$ nm; $\epsilon=29500$ ($H_2O$).

The diethyl (4-chlorophenyl)methanephosphonate used as starting material is obtained as follows:

With stirring, 495 g of 4-chlorobenzylchloride and 1531 g of triethyl phosphite are slowly heated to 150° C. and the mixture is stirred for 7 hours at this temperature. Excess triethyl phosphite is then distilled off in a water jet vacuum, affording 800 g of a pale yellow oil containing 98.8% of diethyl (4-chlorophenyl)methanephosphonate.

EXAMPLE 2

63.4 g of compound (100) are dissolved at 95° C. in 100 ml of demineralised water. Then 23 g of potassium chloride are added and the mixture is cooled to room temperature. The crystalline precipitate is filtered with suction and washed with 5% potassium chloride solution. The moist filter cake is dissolved at 95° C. in 200 ml of demineralised water and then potassium chloride is added in portions until the solution becomes slightly turbid. The solution is allowed to cool and the crystalline precipitate is filtered with suction, washed with 5% potassium chloride solution, then recrystallised first from 200 ml of demineralised water and then from a mixture of 50 ml of demineralised water and 50 ml of ethanol, and dried. Yield: 52 g of the compound of the formula

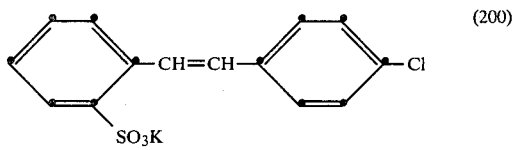

(200)

in the form of a white crystalline powder which still contains 3.8% of water of crystallisation. UV spectrum: $\lambda_{max.} = 302$ nm ($H_2O$).

EXAMPLE 3

With stirring, 52.5 g of diethyl (4-chlorophenyl)methanephosphonate (98.8%) and 51.2 g of the sodium salt of 4-chlorobenzaldehyde-3-sulfonic acid (94.7%) are dissolved in 250 ml of dimethyl formamide at 40°–45° C. Then 39.6 g of a 30% methanolic solution of sodium methylate are added dropwise over 20 minutes, while keeping the temperature at 40°–45° C. The reaction mixture is then stirred for 3 hours at 40°–45° C. neutralised with hydrochloric acid, and evaporated to dryness in vacuo. The residue is dissolved at 95° C. in 800 ml of demineralised water and the turbid solution is filtered clear. The filtrate is cooled and the crystalline precipitate is filtered with suction, recrystallised from 600 ml of demineralised water and vacuum dried at 120° C. Yield: 57 g of the compound of the formula

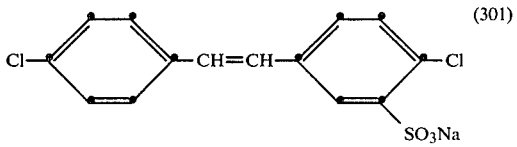

(301)

in the form of white crystals.

UV spectrum $\lambda_{1\ max.} = 305$ nm; $\epsilon = 33'000$ } (dimethyl
$\lambda_{2\ max.} = 320$ nm; $\epsilon = 35'000$ } formamide/$H_2O = 1:1$)

The following compounds can be obtained in similar manner using the corresponding benzaldehydesulfonic acids:

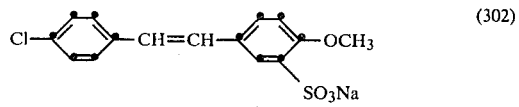

(302)

White crystals.

UV spectrum: $\lambda_{1\ max.} = 304$ nm; $\epsilon = 31'000$ } (dimethyl
$\lambda_{2\ max.} = 319$ nm; $\epsilon = 30'500$ } formamide/$H_2O = 1:1$)

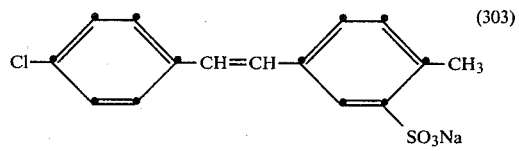

(303)

White crystals

UV spectrum: $\lambda_{1\ max.} = 305$ nm; $\epsilon = 32'000$ } (dimethyl
$\lambda_{2\ max.} = 316$ nm; $\epsilon = 33'000$ } formamide/$H_2O = 1:1$)

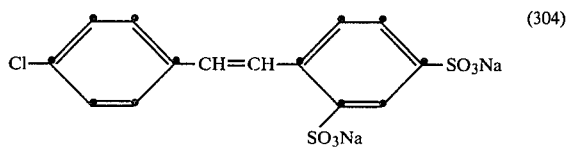

(304)

White crystals

UV spectrum: $\lambda_{max.} = 316$nm; $\ominus = 33'500$ (dimethyl formamide/$H_2O = 1:1$)

EXAMPLE 4

With stirring, 121 g of diethyl (4-bromophenyl)methanephosphonate (98.5%) and 88.5 g of the sodium salt of benzaldehyde-2-sulfonic acid (94.5%) are dissolved in 400 ml of dimethyl formamide. Then 79 g of a 30% methanolic solution of sodium methylate are added dropwise over 30 minutes, whereupon the temperature rises to 48° C. The reaction mixture is then stirred for 3 hours at 40°–50° C., neutralised with acetic acid, and evaporated to dryness in vacuo. The residue is recrystallised twice from 600 ml of demineralised water, affording 106 g of the compound of the formula

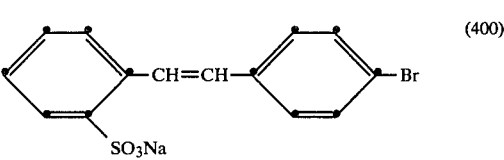

(400)

in the form of white crystals.

UV spectrum: $\lambda_{1\ max.} = 305$ nm; $\epsilon = 30'500$ } (dimethyl
$\lambda_{2\ max.} = 315$ nm; $\epsilon = 30'000$ } formamide/$H_2O = 1:1$)

The diethyl (4-bromophenyl)methanephosphonate used as starting material is obtained as follows:

With stirring, 100 g of 4-bromobenzyl bromide and 300 ml of triethyl phosphite are heated to 140° C. and the mixture is stirred for 3 hours at this temperature. Excess triethyl phosphite is then distilled off in a water jet vacuum, affording 121 g of a pale yellow oil containing 98.5% of diethyl (4-bromophenyl)methanephosphonate.

EXAMPLE 5

16.1 g of compound (100) are dissolved at 75°–80° C. in 70 ml of demineralised water and 18.7 g of a 36% solution of sodium hydroxide in water. After addition of 3 g of 1% palladium on carbon, 72 g of methanol are added dropwise, with stirring, over 3 hours, while the reaction mixture boils under reflux. The reaction mixture is refluxed for a further 21 hours and the palladium on carbon is filtered off hot. The filtrate is neutralised with hydrochloric acid and evaporated to dryness. The residue is dissolved at 90° C. in 100 ml of water and sodium chloride is added to the solution in portions until the product crystallises out. After cooling to 5° C., the crystalline precipitate is filtered with suction, washed with 10% sodium chloride solution and vacuum dried at 120° C. Yield: 11.3 g of a pale yellow crystal powder which contains 29.2% of the compound of the formula

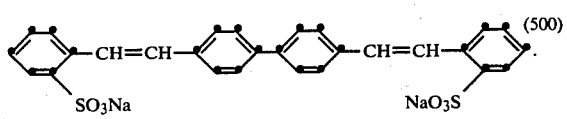
(500)

What is claimed is:
1. A silbene compound of the formula

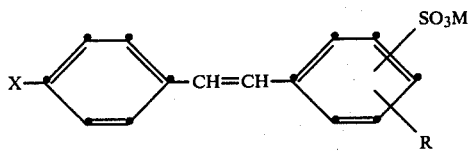

wherein X is halogen, R is hydrogen, —SO$_3$M, halogen, C$_1$–C$_4$alkyl or C$_1$–C$_4$alkoxy, and M is hydrogen or a salt-forming cation.

2. A stilbene compound according to claim 1 of the formula

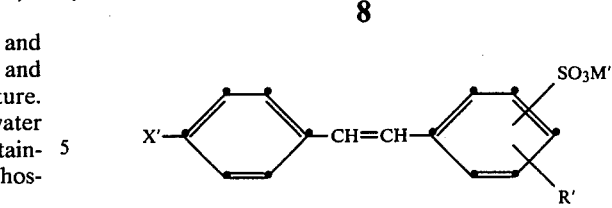

wherein X' is chlorine or bromine, R' is hydrogen, —SO$_3$M', chlorine, bromine, C$_1$–C$_4$alkyl or C$_1$–C$_4$alkoxy, and M' is an alkali metal ion, an ammonium ion or an amine salt ion.

3. A stilbene compound according to claim 2 of the formula

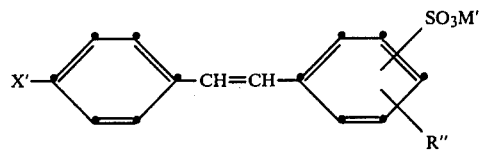

wherein X' is chlorine or bromine, R" is hydrogen, chlorine, methyl or methoxy, and M' is an alkali metal ion, an ammonium ion or an amine salt ion.

4. A stilbene compound according to claim 3 of the formula

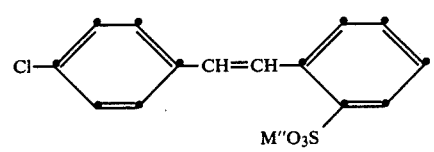

wherein M" is sodium or potassium.

5. A stilbene compound according to claim 3 of the formula

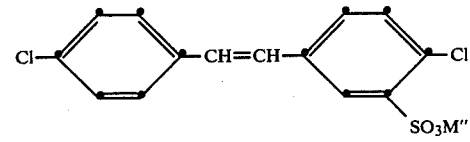

wherein M" is sodium or potassium.

* * * * *

UNITED STATES PATENT AND TRADEMARK OFFICE
CERTIFICATE OF CORRECTION

PATENT NO. : 4,424,170
DATED : January 3, 1984
INVENTOR(S) : Kurt Weber

It is certified that error appears in the above-identified patent and that said Letters Patent is hereby corrected as shown below:

Claim 1, column 7, line 35 reads-A silbene compound of the formula.

Should read -- A stilbene compound of the formula --

Signed and Sealed this

Eleventh Day of September 1984

[SEAL]

Attest:

Attesting Officer

GERALD J. MOSSINGHOFF

Commissioner of Patents and Trademarks